(12) United States Patent
Xu

(10) Patent No.: US 8,292,799 B2
(45) Date of Patent: *Oct. 23, 2012

(54) BIOLOGICAL ARTIFICIAL BLOOD VESSEL AND METHOD OF MAKING

(75) Inventor: Guo-Feng Xu, Guangzhou (CN)

(73) Assignee: Grandhope Biotech Co., Ltd. (CN)

( * ) Notice: Subject to any disclaimer, the term of this patent is extended or adjusted under 35 U.S.C. 154(b) by 1439 days.

This patent is subject to a terminal disclaimer.

(21) Appl. No.: 11/494,817

(22) Filed: Jul. 28, 2006

(65) Prior Publication Data

US 2007/0027529 A1    Feb. 1, 2007

(30) Foreign Application Priority Data

Jul. 29, 2005   (CN) .......................... 2005 1 0036175

(51) Int. Cl.
*A61F 2/06* (2006.01)
(52) U.S. Cl. ......................................................... 600/36
(58) Field of Classification Search ............ 600/36; 623/1.1–1.54
See application file for complete search history.

(56) References Cited

U.S. PATENT DOCUMENTS

| | | | |
|---|---|---|---|
| 3,802,437 A | 4/1974 | Kees, Jr. | |
| 3,974,526 A | 8/1976 | Dardik et al. | |
| 4,083,066 A | 4/1978 | Schmitz et al. | |
| 4,319,363 A | 3/1982 | Ketharanathan | |
| 4,481,009 A | 11/1984 | Nashef | |
| 4,597,766 A | 7/1986 | Hilal et al. | |
| 4,765,335 A | 8/1988 | Schmidt et al. | |
| 4,793,344 A | 12/1988 | Cumming et al. | |
| 5,067,962 A | 11/1991 | Campbell et al. | |
| 5,078,744 A | 1/1992 | Chvapil | |
| 5,080,670 A | 1/1992 | Imamura et al. | |
| 5,217,492 A | 6/1993 | Guire et al. | |
| 5,290,217 A | 3/1994 | Campos | |
| 5,416,074 A | 5/1995 | Rabaud et al. | |
| 5,447,536 A | 9/1995 | Girardot et al. | |
| 5,549,666 A | 8/1996 | Hata et al. | |
| 5,733,339 A | 3/1998 | Girardot et al. | |
| 5,741,283 A | 4/1998 | Fahy | |
| 5,758,420 A | 6/1998 | Schmidt et al. | |
| 5,891,196 A * | 4/1999 | Lee et al. | 8/94.11 |
| 5,902,338 A | 5/1999 | Stone | |
| 5,955,110 A | 9/1999 | Patel et al. | |

(Continued)

FOREIGN PATENT DOCUMENTS

CN    1445003    5/1999

(Continued)

OTHER PUBLICATIONS

Harada O, Kadota K, Yamamoto T. Collagen-Based New Biomedicial Films: Synthesis, Property, and Cell Adhesion. Journal of Applied Polymer Science 81: 2433-2438, 2001.*

(Continued)

*Primary Examiner* — Charles A Marmor, II
*Assistant Examiner* — Catherine E Burk
(74) *Attorney, Agent, or Firm* — Raymond Sun

(57) ABSTRACT

A prosthetic device for implantation into a human body is made by a method that includes the steps of providing a natural animal tissue that has a substrate, crosslinking and fixing the substrate, minimizing the antigens from the substrate, tanning the substrate to improve its mechanical properties, and coupling an anticoagulant to an inner surface of the substrate to form an anticoagulant surface layer.

16 Claims, 2 Drawing Sheets

U.S. PATENT DOCUMENTS

| | | | |
|---|---|---|---|
| 5,976,192 A | 11/1999 | McIntyre et al. | |
| 5,984,858 A | 11/1999 | Stone | |
| 6,008,292 A | 12/1999 | Lee et al. | |
| 6,090,995 A | 7/2000 | Reich et al. | |
| 6,106,555 A * | 8/2000 | Yang | 623/11.11 |
| 6,117,979 A * | 9/2000 | Hendriks et al. | 530/356 |
| 6,177,514 B1 | 1/2001 | Pathak et al. | |
| 6,241,981 B1 | 6/2001 | Cobb et al. | |
| 6,251,117 B1 | 6/2001 | Kringel et al. | |
| 6,391,538 B1 * | 5/2002 | Vyavahare et al. | 435/1.1 |
| 6,458,889 B1 | 10/2002 | Trolisas et al. | |
| 6,482,584 B1 | 11/2002 | Mills et al. | |
| 6,572,650 B1 | 6/2003 | Abraham et al. | |
| 7,053,051 B2 | 5/2006 | Hendriks et al. | |
| 7,060,103 B2 | 6/2006 | Carr, Jr. et al. | |
| 7,077,851 B2 | 7/2006 | Lutze et al. | |
| 7,674,289 B2 * | 3/2010 | Xu | 623/13.17 |
| 7,820,871 B2 | 10/2010 | Xu | |
| 7,824,447 B2 * | 11/2010 | Xu | 8/94.1 R |
| 2001/0031743 A1 | 10/2001 | Peterson et al. | |
| 2002/0042473 A1 | 4/2002 | Trolisas et al. | |
| 2002/0081564 A1 | 6/2002 | Levy et al. | |
| 2002/0091445 A1 | 7/2002 | Sung et al. | |
| 2002/0095218 A1 * | 7/2002 | Carr et al. | 623/23.72 |
| 2002/0099448 A1 | 7/2002 | Hiles et al. | |
| 2002/0103542 A1 | 8/2002 | Bilbo | |
| 2002/0138152 A1 | 9/2002 | Francis et al. | |
| 2003/0013989 A1 | 1/2003 | Obermiller et al. | |
| 2004/0038257 A1 * | 2/2004 | Ishii et al. | 435/6 |
| 2004/0202625 A1 | 10/2004 | Daniloff et al. | |
| 2005/0119736 A1 | 6/2005 | Zilla et al. | |
| 2005/0136543 A1 | 6/2005 | Torres et al. | |
| 2005/0187140 A1 | 8/2005 | Hunter et al. | |
| 2005/0229323 A1 | 10/2005 | Mills et al. | |
| 2008/0195229 A1 | 8/2008 | Quijano et al. | |

FOREIGN PATENT DOCUMENTS

| | | |
|---|---|---|
| CN | 1237889 | 12/1999 |
| CN | 1267201 | 9/2000 |
| CN | 1313741 | 9/2001 |
| CN | 1330528 | 1/2002 |
| CN | 1456363 | 11/2003 |
| CN | 1473551 | 2/2004 |
| CN | 1556715 | 12/2004 |
| CN | 1579342 | 2/2005 |
| WO | WO9417851 | 8/1994 |
| WO | WO 9822158 | 5/1998 |
| WO | WO 0032250 | 6/2000 |
| WO | WO0232327 | 4/2002 |

OTHER PUBLICATIONS

Rouet V, Hamma-Kourbali Y, Petit E, Panagopoulou P, Katsoris P, Barritault D, Caruelle JP, Courty J. J Biol Chem 280(38), p. 32792-32800, Sep. 23, 2005.*

IPR—PCT/CN2006/003419.
IPR—PCT/CN2006/003442.
IPR—PCT/CN2006/003443.
IPR—PCT/CN2006/003444.
IPR—PCT/CN2006/001878.
IPR—PCT/CN2006/001879.
IPR—PCT/CN2006/001880.

* cited by examiner

BIOLOGICAL ARTIFICIAL BLOOD VESSEL AND METHOD OF MAKING

BACKGROUND OF THE INVENTION

1. Field of the Invention

The present invention relates to a medical prosthesis for human implantation, and in particular, to an artificial blood vessel which is utilized to replace damaged blood vessels, or as a device for bypassing blood vessels.

2. Description of the Prior Art

Vascular diseases have become one of the most important diseases that threaten human health and life. An important method for treating vascular diseases is to use an artificial blood vessel to replace the diseased blood vessel, or to bypass the diseased portion of the vessel. Currently, the most commonly-used artificial blood vessels for clinical application are knitted Dacron tubes or expanded polytetrafluoroethylene tubes, both being produced from synthetic materials which can be used to form internal pseudomembranes and to maintain long-term smooth passage of blood. Unfortunately, all foreign matters that are implanted into a human body face some degree of chronic rejection sooner or later, which can lead to an adverse reaction in the body. In addition, the anticoagulation of these conventional artificial blood vessels is poor, and usually only artificial blood vessels having a diameter of at least a 6 mm provide good passage, so that smaller-diameter artificial blood vessels, especially those having diameters of less than 4 mm, often result in embolisms after being implanted.

There have been many studies using animal blood vessels as artificial blood vessels for humans, but none have become a viable product for clinical application because the techniques for treatment are out-of-date. For example, the conventional treatment methods include fixing an animal blood vessel with glutaraldehyde, followed by defatting and cell removal, and then the product is directly implanted. Treatment with glutaraldehyde is for fixing the protein molecules in the animal tissue through crosslinking by the acetal reaction, but toxic glutaraldehyde is slowly released due to degradation after the animal blood vessel treated in this manner is implanted into a human body, thereby inhibiting the production of endothelial cells in the blood vessel. In addition, the conventional treatment method employs cell removal as an effective means for eliminating or removing antigens, but according to research results in molecular biology and molecular immunology, antigenicity does not only originate from the cell, but also from active groups at certain specific locations on the proteins and polysaccharides, or specific conformations. These specific groups or conformations are called antigenic determinants clusters, and antigens can only be eliminated by blocking the active groups of the antigenic determinants and altering the specific conformation of the antigenic determinants; antigens cannot be effectively eliminated by cell removal.

Accordingly, the conventional methods for treating animal blood vessels do not totally eradicate chronic immune rejection due to the toxic presence of residual glutaraldehyde and the incomplete elimination of the antigens, making it very difficult for the endothelial cells and other vascular cells of the host blood vessels to migrate and grow into the artificial blood vessel, so that the expected effects cannot be attained.

SUMMARY OF THE DISCLOSURE

It is an object of the present invention to provide a biological artificial blood vessel that overcomes the disadvantages described above, while having good biocompatibility, minimal residual toxicity and minimal chronic delayed immune rejection.

It is another object of the present invention to provide a method of preparing a biological artificial blood vessel that overcomes the disadvantages described above, while having good biocompatibility, minimal residual toxicity and minimal chronic delayed immune rejection.

In order to accomplish the objects of the present invention, the present invention provides a prosthetic device for implantation into a human body. The prosthetic device is made by a method that includes the steps of:

1. providing a natural animal tissue that has a substrate;
2. crosslinking and fixing the substrate;
3. minimizing the antigens from the substrate;
4. tanning the substrate to improve its mechanical properties; and
5. coupling an anticoagulant to an inner surface of the substrate to form an anticoagulant surface layer.

DETAILED DESCRIPTION OF THE PREFERRED EMBODIMENTS

Figure 1:
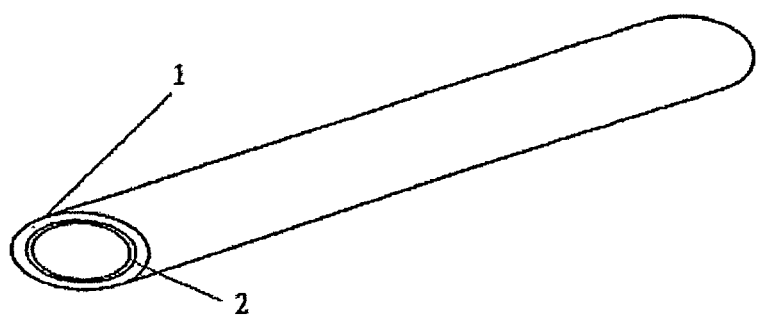
FIG. 1 is a perspective view of an artificial blood vessel according to one embodiment of the present invention.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention provides a biological artificial blood vessel having a substrate made of an animal blood vessel that is crosslinked and fixed with a fixative, treated to minimize antigens, subjected to a tanning process, and then coated with a surface layer containing an anticoagulant bound to the inner surface of the substrate.

The surface layer can also include an active layer. Although the present invention is being described in connection with animal blood vessels, the principles of the present invention also apply to the various applications described at the end of this disclosure.

Animal blood vessel tissues comprise mainly collagens and glucosaminoglycans which are easily degraded or decomposed by microorganisms. Conventionally, aldehydes (formaldehyde, glutaraldehyde, etc.) are utilized for crosslinking and fixation to increase their stability. However, aldehydes undergo crosslinking with proteins through the acetal reaction and toxic aldehydes are released when the crosslinked products are degraded, so that products fixed with an aldehyde have long-term residual toxicity. When epoxides, diamides, diisocyanates or carbodiimides are utilized as fixatives in place of aldehydes, this toxicity problem can be eliminated. When an epoxide is utilized, for example, proteins are crosslinked through the ring opening reaction of the epoxide, and reverse ring closure to form the epoxide back does not readily occur, and the degradation products are polyols which can be metabolized by the body so that there is no risk of toxic aldehyde radicals. The stability of the animal blood vessels after treatment is also higher than those fixed with aldehydes. According to modern immunological theory, the antigenicity of animal tissues stems mainly from active groups located at specific sites and in specific conformations, and these active groups include —OH, —NH2, —SH, etc. The specific conformations result mainly from some specific hydrogen bonding formed by spiral protein chains. The specific sites and conformations are called antigen determinants. When treating the animal blood vessels, one or several small, active reagents (e.g., acid anhydrides, acid chlorides, acylamides, epoxides, etc.) which can readily react with these groups are used to bind and block these groups, which in turn effectively minimizes the antigenicity, and in the meantime strong hydrogen bonding reagents (e.g., guanidine compounds) are utilized to form new hydrogen bonds and replace the inherent hydrogen bonding of the specific conformations, which changes the specific conformations and further effectively minimizes the antigenicity. The tissues of the animal vessels cannot be easily altered after they have been crosslinked and fixed by epoxides, thereby leaving no residual toxicity. The immunogenicity is effectively minimized by blocking the active groups in the proteins and changing the conformation, and the resulting substrate has no chronic immune rejection while having excellent biocompatibility.

Tanning

The present invention uses an additional cross-linking method and a protein grafting method as a tanning process to improve the mechanical strength and toughness of the tissue. In this regard, a piece of animal blood vessel (especially a vein, or artery with cell removal) usually provides poor mechanical properties (after harvesting). As used herein, "mechanical properties" means strength, toughness, rigidity and modulus. Both cross-linking and protein grafting can alter the mechanical properties of the tissue collagen (protein) matrix. Although cross-linking and protein grafting are common methods that are used to improve the mechanical properties of high polymers, it is still important to carefully determine the selection of reagents as well as the reaction conditions because protein can often be denatured. The length, density and distribution of cross-linkage are properly designed to ensure the stability of the tissue material and mechanical property.

For example, the molecular chain length of the crosslinking agent determines the cross-linking length. A longer chain results in better material flexibility. However, larger molecular chains are more difficult to penetrate into the collagen matrix. For example, when selecting an epoxy compound as the cross-linking agent, the molecular chain is preferably 4-8 hydrocarbons. The cross-linking density determines the cross-linking degree. Denser cross-linking results in better material stability, but denser cross-linking (especially when combined with a shorter molecular chain) can introduce a higher local stress in the material. A relatively uniform distribution of the cross-linking is ideal, but is usually difficult to obtain. Utilizing a lower concentration of the cross-linking solution, under a lower temperature, longer reaction duration, and repeating a few more times with the same reaction can often yield better results. As an example, when using an epoxy compound as the cross-linking agent as described in U.S. Pat. No. 6,106,555, good material stability, good flexibility, toughness and strength can be obtained by picking 4-8 hydrocarbon atom chain, with a concentration of 0.1 to 2%, under 4 to 24 degrees Celcius, reaction for 3-10 days, and repeating 2 to 5 times.

The chemical reagents can be the same as those described herein for use with tissue fixation. The protein grafting process can further improve the tissue's mechanical strength, toughness, rigidity and modulus. Protein grafting requires a large amount of polymer chains so that the nature of the protein structure can be changed substantially. Some high polymers can be grafted into collagen molecules by means of polycondensative primers. In order to avoid introducing hazardous subject matter into the human body, it is preferable to use biodegradable high polymers as the grafting agents, such as polyglycolic acid (PGA), polylactic acid (PLA) and others. These biodegradable polymers can be metabolized in the host environment through a tracarboxylic acid cycle just like for carbohydrates or fat metabolism. After such an extensive protein modification, up to 25 kGy gamma ray sterilization can be applied without adversely affecting the mechanical property of the tissue material. The total amount of protein grafting can be controlled optimally.

Because the surface layer containing an anticoagulant is chemically bonded to the inner surface of the substrate, which prevents the layer from being washed away by the blood, the anticoagulant effect can be maintained for a long time and unimpeded passage of the blood can be ensured for a long time after implantation.

Active Layer

The surface layer can also include an active layer. This active layer can contain a specific polypeptide capable of adhering to and accumulating growth factors, so that angiogenesis can be promoted. Examples of growth factors for blood vessels that can adhere to and accumulate include vascular endothelial growth factor (VEGF), fibroblast growth factor (FGF), platelet-derived growth factor (PDGF-bb) and vascular permeability factor (VPF). One example of the polypeptide is the polypeptide consisting of 16 lysines (K16), glycine (G), arginine (R), aspartic acid (D), serine (S), proline (P) and cysteine (C), and sequence of the composition is K16-G-R-G-D-S—P—C.

As illustrated in the Examples below, the substrate of the artificial blood vessel of the present invention can be shaped as a straight tube, or a U tube, or a C tube, or a Y tube, for convenient implantation in different applications.

Method

A method of preparing the biological artificial blood vessels according to the present invention comprises the following steps, using natural animal blood vessels as the substrate:

1. Pretreatment: Initial sterilization is performed using a broad spectrum, highly-effective, low-toxicity bacteriacide, followed by trimming excess tissues.

2. Defatting: The fatty substances in the substrate are extracted with organic solvents using known tissue-treatment techniques.

3. Fixation: The protein molecules in the substrate are crosslinked and fixed using a fixative, as described in greater detail hereinbelow.

4. Minimizing antigens: An active reagent is utilized to block the specific active groups such as —OH, —NH2, —SH, etc., in the proteins of the substrate, and a reagent with strong hydrogen bonding power is utilized to replace the specific hydrogen bonding in the spiral chains of the protein molecules in the substrate and alter its specific conformation.

5. Tanning process: First, the preformed polymers are produced from monomers by synthesis. Second, the substrate is dehydrated with alcohol. Third, the preformed polymers are then grafted into collagen molecules by means of polycondensative primers. When using PGA as the grafting reagent, a small amount of glycolide may be used as the polycondensative primer. When using PLA as the grafting reagent, a small amount of lactide may be used as the polycondensative primer.

For example, using PLA as the protein grafting agent, the process could take 30-50 mg of lactide and dissolve it in 1000 ml of chloroform. 2-3 grams of triisobutyl aluminum can be added as the composite catalyst, and this solution can be stir-mixed for one to two hours under a temperature of 40-60 degrees Celcius. 100 ml of a 0.1N NaOH solution is then added and stir-mixed for 30-60 minutes to destroy the catalyst. Then take away the separated water layer (with catalyst) and have the preformed polymers ready. Immerse the dehydrated substrate into the preformed polymer solution. Add 0.1 to 2 g of lactide and 0.5 to 5 g of proprionic anhydride as an initiation catalyst and then stir-mix for 2-4 hours under a temperature of 34 to 40 degrees Celcius. Take out the substrate and put it into chloroform to clean away the residual preformed polymers. After rinsing with saline, the substrate is then immersed into saline for 12 to 24 hours to recover the water content. The substrate is now ready for the next processing step.

6. Anticoagulant modification: A coupling agent is utilized to couple an anticoagulant to the inner surface of the substrate to form an anticoagulant surface layer.

7. Coupling of active layer: An active surface layer containing a specific polypeptide or glucosaminoglycan capable of adhering to growth factors is incorporated on the surface layer using a coupling agent. This step is utilized for the optimal design.

Fixative

The fixative applied in step 3 of the above method may be an epoxy compound that has a hydrocarbon backbone, that is water-soluble, and which does not contain an ether or ester linkage in its backbone. This fixative is described in U.S. Pat. No. 6,106,555, whose entire disclosure is incorporated by this reference as though set forth fully herein. Examples include an epoxide, a diamide, a diisocyanate, or a carbodiimide, in that the epoxide may be a monocyclic epoxide, or a bicyclic epoxide, or it may be a low poly(epoxide) (such as low poly (ethylene oxide), poly(propylene oxide) or a glycidyl ether).

Active Reagents

The active reagents in step 4 of the above method may be low molecular weight organic acid anhydrides, acyl chlorides, acylamides or monocyclic oxides, and the reagents having strong hydrogen bonding power are guanidine compounds.

Anticoagulants

The anticoagulants agents in step 5 of the above method may be substances carrying a negative charge on the surface layer, but an excessively strong negative charge on the surface is detrimental to the growth and proliferation in the blood vessels of the endothelial cells (which also carry a negative charge). For this reason, heparin is the preferred anticoagulant according to one embodiment of the present invention. or the strong anticoagulant heparin. The coupling agents utilized may be epoxides, acid anhydrides or diacyl chlorides.

Coupling Agent for Active Layer

The coupling agent utilized for coupling the polypeptide in step 7 of the above method may be a diamide, acid anhydride or bicyclic oxide, or other bifunctional reagent capable of undergoing a condensation reaction with —NH2, —OH, —COOH, etc.

The present invention provides the following advantages. After treatment according to the above method, the animal blood vessels are very stable and antigens are completely eliminated, causing no rejection and having good biocompatibility with blood and little coagulation with ensured long-term unimpeded passage of blood after implantation. Because the basic composition resembles that of the human body and the final degradation products are the 20 amino acids constituting biological proteins and glycoproteins, they can be absorbed and utilized by the human body. The biocompatibility of the tissue of the animal blood vessel is good so that the blood vessels are an excellent support for angiogenesis, and are capable of inducing the growth of new blood vessel tissues in them. The polypeptide can accumulate many growth factors to promote the growth of endothelial cells and the formation of new blood vessels, so that the artificial blood vessels are eventually converted into new blood vessel tissue in the human body. The properties of the animal blood vessels of the present invention are significantly better than those of the artificial blood vessels that use synthetic materials, and the animal blood vessels of the present invention are particularly suitable for preparing artificial blood vessels having a diameter of 6 mm or less.

EXAMPLE 1

Figure 2:
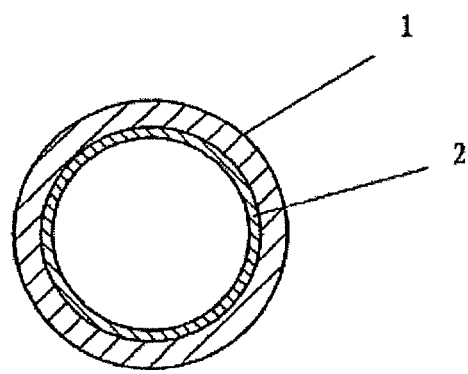
FIG. 2 is a cross-sectional view of the artificial blood vessel of FIG. 1.

Referring to FIGS. 1 and 2, the biological artificial blood vessel according to the present invention has a substrate 1 comprising a natural animal blood vessel that has been crosslinked and fixed with an epoxide, treated to minimize antigens, and including a surface layer 2 bound to the inner surface of substrate 1 and containing an anticoagulant component. The substrate can be a straight tube and the anticoagulant agent in the surface layer 2 is heparin. The surface layer 2 also contains a polypeptide consisting of 16 lysines (K16), glycine (G), arginine (R), aspartic acid (D), serine (S), proline (P) and cysteine (C). This biological artificial blood vessel can be made from the following steps:

1. Pretreatment: Initial sterilization is performed using a broad spectrum, highly-effective, low-toxicity bacteriacide such as benzalkonium chloride or chlorhexidine, followed by trimming excess tissue.

2. Defatting: The fatty substances in the substrate 1 are extracted with an organic solvent such as chloroform, ethyl acetate, anhydrous alcohol or mixtures thereof.

3. Fixation: The protein molecules in substrate 1 are crosslinked and fixed using a bicyclic epoxide.

4. Minimizing antigens: An active reagent such as a low molecular weight organic acid anhydride, acyl chloride, acylamide or monocyclic oxide is utilized to block the specific active groups such as —OH, —NH2, —SH, etc., in the proteins of the substrate 1, and a reagent having strong hydrogen bonding power such as a guanidine compound is utilized to replace the specific hydrogen bonding on the spiral chains of the protein molecules in the substrate 1 and alter its specific conformation.

5. Tanning process: Utilizing PLA as the grafting reagent, a small amount of lactide is used as the polycondensative primer.

6. Anticoagulant modification: A coupling agent is utilized to couple the anticoagulant (heparin) to the inner surface of the substrate 1 to form the anticoagulant surface layer 2.

7. Coupling polypeptide: A diamide is utilized as a coupling agent to couple a polypeptide consisting of 16 lysines (K16), glycine (G), arginine (R), aspartic acid (D), serine (S), proline (P) and cysteine (C) capable of binding a wide variety of growth factors on surface layer 2, and the sequence of the composition of the polypeptide is K16-G-R-G-D-S—P—C.

EXAMPLE 2

Figure 3:
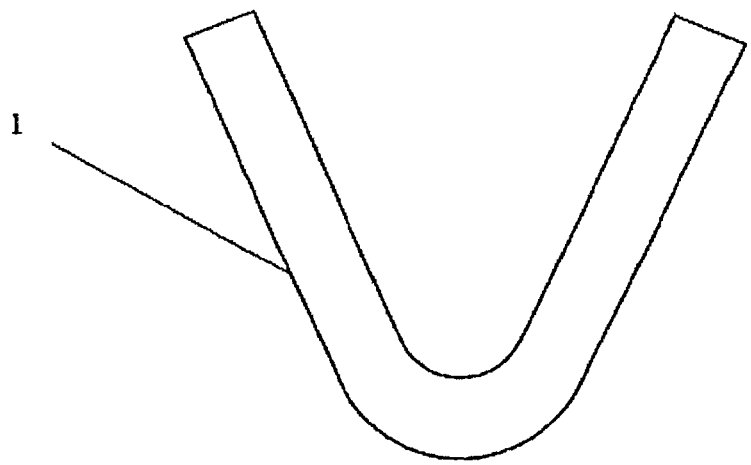
FIGS. 3-5 illustrates artificial blood vessels according to other embodiments of the present invention.

Referring to FIG. 3, the substrate 1a is a U tube and a diisocyanate is utilized for fixing the protein molecules while all the other technical characteristics are the same as those of Example 1.

EXAMPLE 3

Figure 4:
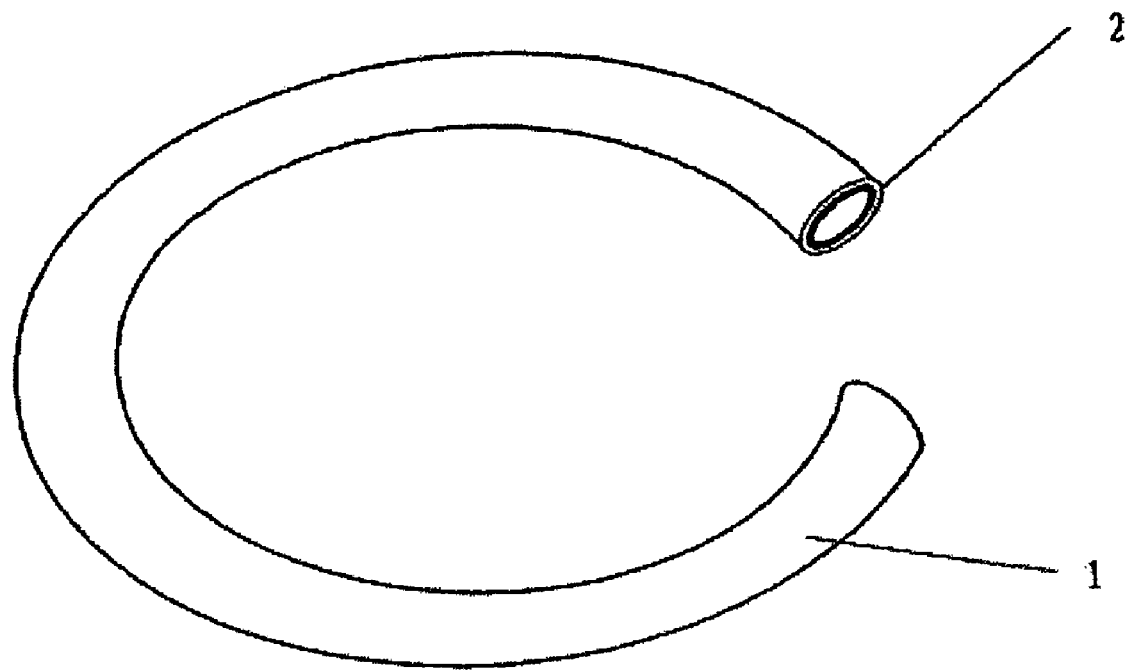

Referring to FIG. 4, the substrate 1b is a C tube and a diamide is utilized for fixing the protein molecules while all other technical characteristics are the same as those of Example 1.

EXAMPLE 4

Figure 5:
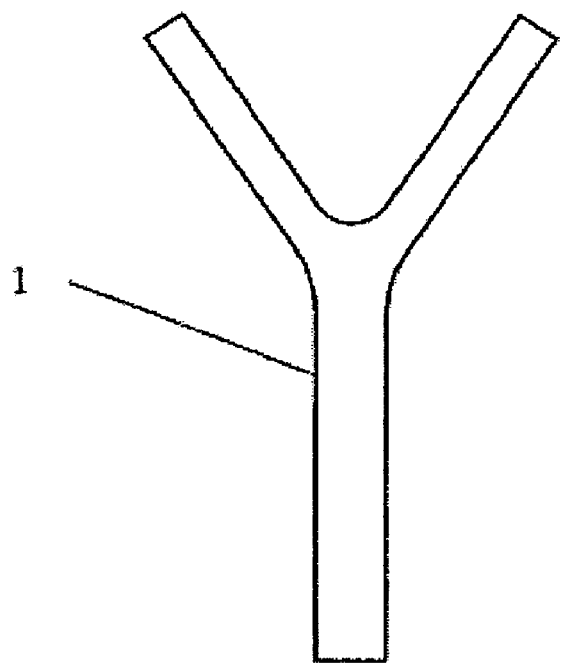

Referring to FIG. 5, the substrate 1c is a Y tube while all other technical characteristics are the same as those of Example 1.

Other Applications

The method of the present invention can also be utilized to treat a variety of other prosthetic devices.

For example, the method of the present invention can be utilized for biological heart valves made from animal aortic valves, pericardiums or other similar membranes, and for cardiovascular surgical repair patches made from animal pericardium or other similar membranes. All the elements, chemicals and steps described herein can be utilized for these two applications.

In addition, the method of the present invention can be utilized for the following applications, with the modification that the anticoagulant is omit:

1. prosthetic urethra and ureter, using animal arteries;
2. prosthetic esophagus, using animal arteries;
3. prosthetic trachea, using animal arteries;
4. hernia repair patch, using animal pericardium or other similar membranes; and
5. stress support sling for urinary incontinence, using animal pericardium or other similar membranes.

Again, all the elements, chemicals and steps described herein can be utilized for these five applications, except that the anticoagulant is omitted.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A method of preparing a vascular graft for implantation into a human body, comprising the steps of:
    isolating from a host a natural animal blood vessel that has a substrate that has —OH, —NH2, —SH groups;
    crosslinking and fixing the —OH, —NH2,—SH groups of the substrate;
    blocking residual specific active —OH, —NH2, —SH groups in protein molecules of the substrate after fixation by applying at least one active reagent;
    altering the specific conformation of protein molecules of the substrate by a reagent with strong hydrogen bonding power; and
    coupling an active layer to the substrate that includes either a polypeptide or a glucosaminoglycan that has the ability to adhere growth factors after implantation.

2. The method of claim 1, wherein the at least one active reagent to block specific active groups in the protein molecules of the substrate can be acid anhydrides, acid chlorides, or acylamides.

3. The method of claim 1, wherein the reagent with strong hydrogen bonding power is a guanidine compound.

4. The method of claim 1, wherein the crosslinking and fixing step includes applying an epoxy compound, a diamide, a diisocyanate, or a carbodiimide.

5. The method of claim 4, wherein the epoxy compound that has a hydrocarbon backbone, that is water-soluble, and which does not contain an ether or ester linkage in its backbone.

6. The method of claim 1, further including:
    coupling an anticoagulant to the inner surface of the substrate to form an anticoagulant surface layer.

7. The method of claim 1, further including, prior to crosslinking and fixing:
    performing initial sterilization on the substrate; and
    extracting fatty substances from the substrate.

8. The method of claim 1, further including the step of tanning the substrate.

9. The method of claim 8, wherein the step of tanning the substrate includes:
    producing polymers from monomers; and
    grafting the polymers into collagen molecules.

10. The method of claim 1, wherein altering the specific conformation of protein molecules of the substrate by a reagent with strong hydrogen bonding power forms new hydrogen bonds and replaces the inherent hydrogen bonding of the specific conformations.

11. A vascular graft for implantation into a human body, comprising a natural animal blood vessel isolated from its host that has a substrate that has: (i) —OH, —NH2, —SH groups which have been fixed with crosslinking reagents, (ii) residual specific active —OH, —NH2, —SH groups in protein molecules of the substrate that have been blocked by at least one active reagent after fixation by the crosslinking reagents, (iii) specific conformation of protein molecules of the substrate altered by a reagent with strong hydrogen bonding power, and (iv) an active layer coupled thereto, the active layer including either a polypeptide or a glucosaminoglycan that has the ability to adhere growth factors after implantation.

12. The graft of claim 11, wherein the at least one active reagent to block specific active groups in the protein molecules of the substrate can be acid anhydrides, acid chlorides, or acylamides.

13. The graft of claim 11, wherein the reagent with strong hydrogen bonding power is a guanidine compound.

14. The graft of claim 11, wherein the substrate is fixed by an epoxy compound, a diamide, a diisocyanate, or a carbodiimide.

15. The graft of claim 14, wherein the epoxy compound has a hydrocarbon backbone, is water-soluble, and which does not contain an ether or ester linkage in its backbone.

16. The graft of claim 11, wherein the specific conformation of protein molecules of the substrate is altered by a reagent with strong hydrogen bonding power to form new hydrogen bonds and replace the inherent hydrogen bonding of the specific conformations.

* * * * *